United States Patent [19]
Gibbons et al.

[11] 3,983,246
[45] Sept. 28, 1976

[54] N-(SULFONYLOXY) BENZIMIDOYL HALIDES AS BACTERICIDAL OR FUNGICIDAL AGENTS

[75] Inventors: Loren Kenneth Gibbons; Clinton Joseph Peake; Wayne Nelson Harnish, all of Medina, N.Y.

[73] Assignee: FMC Corporation, Philadelphia, Pa.

[22] Filed: Apr. 4, 1974

[21] Appl. No.: 457,989

[52] U.S. Cl. .......................... 424/303; 260/566 AE; 424/282; 424/DIG. 8
[51] Int. Cl.$^2$ ....................... A01N 9/14; A01N 9/18
[58] Field of Search ..................... 424/DIG. 8, 303; 260/566 AE

[56] References Cited
OTHER PUBLICATIONS

King et al., Can. J. Chem., 44, 409–411 (1966).

Truce et al., Can. J. Chem., 44, 297–305 (1966).

Rajagopalan et al., Tetrahedron Letters, 1966, No. 19, pp. 2101–2108.

Fernandes et al., Chemotherapia, 12, 186–296 (1967).

Primary Examiner—James O. Thomas, Jr.
Assistant Examiner—Allen J. Robinson

[57] ABSTRACT

Agricultural fungicidal compositions based on N-(sulfonyloxy)benzimidoyl halides exhibit a broad spectrum of antifungal activity, particularly against late blight, bean rust and rice blast. The synthesis of representative compounds is described, and the utility of antifungal compositions is exemplified.

8 Claims, No Drawings

N-(SULFONYLOXY) BENZIMIDOYL HALIDES AS BACTERICIDAL OR FUNGICIDAL AGENTS

The present invention pertains to the general field of agricultural pesticides, particularly to agricultural fungicidal compositions having a broad spectrum of activity, and which are active especially against late blight, bean rust and rice blast.

Preparation of N-(methanesulfonyloxy)benzimidoyl chloride was reported by J. F. King and T. Durst, Can. J. Chem. 44, 409-411 (1966), by W. E. Truce and A. R. Naik, Can. J. Chem. 44, 297-305 (1966), and by P. Rajagopalan and C. N. Talaty, Tetrahedron Letters 1966, No. 19, 2101–2108; also reported were preparations of N-(methanesulfonyloxy)benzimidoyl chloride with 4-chloro-, 3,4-dichloro-, and 3-nitro- substituents in the benzene nucleus. None of these disclosures contained any suggestion of fungicidal utility.

Tests of these compounds against fungi and bacteria in vitro, reported by F. Fernandes, F. X. R. Costa Percira, and R. M. Desai, Chemotherapia 12, 286–296 (1967), showed N-(methanesulfonyloxy)benzimidoyl chloride and N-(methanesulfonyloxy)-4-chlorobenzimidoyl chloride to be active against the fungus Candida albicans and the bacteria Trichophyton interdigitale and Mycobacterium tuberculosis. N-(Methanesulfonyloxy)-3,4-dichlorobenzimidoyl chloride was active against C. albicans and M. tuberculosis, and N-(methanesulfonyloxy)-3-nitrobenzimidoyl chloride was active against T. interdigitale and M. tuberculosis. A compound combining the substituents of the latter two compounds, N-(methanesulfonyloxy)-3,4-dichloro-5-nitrobenzimidoyl chloride, was superior to any of these compounds against C. albicans and M. tuberculosis in vitro, but inactive against C. albicans in vivo. None of these fungi has significance in agriculture.

No reference has been found which discloses or suggests the outstanding antifungal activity in agricultural applications of the compositions of the present invention.

Antifungal activity is exhibited by compositions comprising as an active ingredient one or more compounds of the general formula:

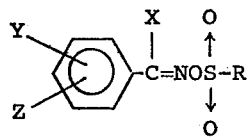

wherein Y is hydrogen, halogen, nitro, alkyl of 1 to 4 carbon atoms or alkoxy of 1 to 4 carbon atoms; Z is hydrogen, chlorine, or may be taken together with Y to form methylenedioxy; X is chlorine or bromine; R is alkyl of 1 to 4 carbon atoms, which may carry a halogen substituent, or allyl.

In preferred embodiments of the present invention, Y is alkyl of 1 to 2 carbon atoms, alkoxy of 1 to 2 carbon atoms, or fluorine; Z is hydrogen; X is chlorine; and R is alkyl of 1 to 4 carbon atoms.

More especially preferred are compounds in which Y is 4-methyl, 4-methoxy, or 4-ethoxy; Z is hydrogen; X is chlorine; and R is methyl, ethyl, or propyl.

Compounds of the present invention are as effective as or more effective than materials previously known as foliar protectants for the contol of late blight, bean rust, and rice blast. Downward systemic activity against Fusarium root rot has been demonstrated.

Active ingredients of the antifungal compositions of the present invention also exhibit miticidal and nematicidal activity.

The active ingredients of the present invention consist of N-(alkanesulfonyloxy)benzimidoyl halides prepared by reaction of benzohydroximoyl halides with alkanesulfonyl halides:

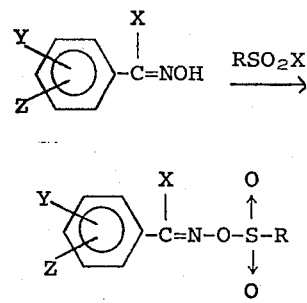

The required benzohydroximoyl chlorides are prepared using known methods from the corresponding benzaldoximes, by reaction with nitrosyl chloride or chlorine, the benzaldoximes having been obtained by reaction of the corresponding substituted aromatic aldehydes with hydroxylamine:

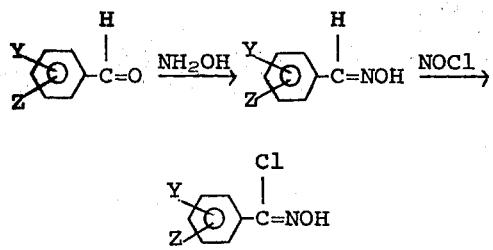

Preparation of representative compounds of the invention and illustration of their pesticidal, particularly antifungal, properties are set forth in the following examples. All proportions in the examples and specification are by weight unless otherwise indicated. All temperatures are in degrees centigrade. All reduced pressures not otherwise designated are the pressures normally attainable using a water aspirator.

EXAMPLE I

N-(Methanesulfonyloxy)-4-methylbenzimidoyl chloride

A. Preparation of 4-methylbenzaldoxime.

Hydroxylamine hydrochloride (41.7 g) in 70 ml of water was added to a solution of 36.1 g of 4-methylbenzaldehyde in 180 ml of absolute ethanol. A solution of 18 g of sodium hydroxide in 36 ml of water was added in portions during 5 to 10 minutes. The reaction mixture was then heated to boiling and filtered hot, and the filtrate was cooled in a dry ice-acetone bath. Water was added to the cooled filtrate until solid product precipitated. The solid was separated by filtration, air-dried overnight, and recrystallized from hexane to give 27.9 g of 4-methylbenzaldoxime, m.p. 73°–77°.

B. Preparation of 4-methylbenzohydroximoyl chloride.

Nitrosyl chloride (15.1 g) was run from a pressure bottle into a methanol-ice cooled Erlenmeyer flask and allowed to distill gradually from there into a mixture of 27.9 g of 4-methylbenzaldoxime and 330 ml of ether contained in a one-liter, three-necked flask equipped with a thermometer, Dewar condenser, and drying tube. During the addition and for several hours afterward, the reaction mixture was kept at about 0°. The reaction mixture was allowed to warm to ambient temperature overnight with stirring. Ether was allowed to evaporate and the oily residue was allowed to solidify under vacuum. The product was recrystallized twice from hexane to give 10 g of 4-methylbenzohydroximoyl chloride, m.p. 71°–74°. The ir spectrum was consistent with the assigned structure.

Analysis: Calc'd for $C_8H_8ClNO$: C, 56.65; H, 4.75; Cl, 20.90; N, 8.26.
Found: C, 56.74; H, 4.97; Cl, 20.96; N, 7.99.

C. N-(Methanesulfonyloxy)-4-methylbenzimidoyl chloride.

4-Methylbenzohydroximoyl chloride (10 g) was dissolved in 160 ml of ether in a one-liter, three-necked flask equipped with a stirrer, thermometer, dropping funnel, and drying tube. The solution was cooled to 0°–4° in a methanol-ice bath, and 8.8 g of triethylamine was added dropwise over a period of about 7 minutes. The mixture was stirred for 5 minutes and a solution of 6.7 g of methanesulfonyl chloride in 16 ml of ether was added dropwise over a period of 30 minutes at 0°–5°. The final mixture was stirred at 0°–5° for 1 hour, then filtered. The collected precipitate was washed several times with ether. The combined filtrate and washes were evaporated and the solid residue formed was recrystallized twice from ethanol to give 1.9 g of N-(methanesulfonylonxy)-4-methylbenzimidoyl chloride, m.p. 101.5°–103.5°. The ir spectrum was consistent with the assigned structure.

Analysis: Calc'd for $C_9H_{10}ClNO_3S$: C, 43.64; H, 4.07; N, 5.66.
Found: C, 43.41; H, 4.17; N, 5.63.

In a second synthesis, 10 g of 4-methylbenzohydroximoyl chloride, 6.7 g of methanesulfonyl chloride, and 160 ml of benzene were mixed in a 250-ml, three-necked, round-bottomed flask equipped with a stirrer, thermometer, and drying tube. Triethylamine (8.8 g) was added dropwise during 6 minutes at 5°–10°, and the mixture was stirred at that temperature for 1 hour. The reaction mixture was filtered, the solid was washed with benzene, the washes and filtrate were combined and concentrated, and the concentrate was recrystallized from ethanol to give 9 g of N-(methanesulfonyloxy)-4-methylbenzimidoyl chloride, m.p. 100°–102°. The ir spectrum was consistent with the assigned structure.

EXAMPLE II

N-(Methanesulfonyloxy)-4-chlorobenzimidoyl chloride

A. Preparation of 4-chlorobenzaldoxime.

To a solution of 50 g of hydroxylamine hydrochloride in 300 ml of water was added a suspension of 20 g of 4-chlorobenzaldehyde in 200 ml of 10% aqueous sodium hydroxide solution. Ethanol was then added until the mixture was clear. The solution was heated on a steam bath for 25 minutes, then cooled in an ice bath. The solid which separated was collected by filtration and dried in a vacuum desiccator. A second fraction was obtained by adding water just to the cloud point. This solid was collected and dried and the two products combined to give 16.75 g of 4-chlorobenzaldoxime, m.p. 108°–109°.

B. Preparation of 4-chlorobenzohydroximoyl chloride.

A solution of 16.75 g of 4-chlorobenzaldoxime in 155 ml of chloroform was cooled to 5°. Chlorine gas was passed slowly through the solution until no more was absorbed; a blue-green color developed and the temperature slowly increased to 20°. The mixture was stirred for 1 hour at 5°, then heated under reflux for half an hour. The mixture was cooled to room temperature, then the solvent was evaporated under reduced pressure to give a white solid. The solid was collected and dried in a vacuum desiccator in a refrigerator at 5° to give 20.4 g of 4-chlorobenzohydroximoyl chloride, m.p. 81°–85°.

C. N-(Methanesulfonyloxy)-4-chlorobenzimidoyl chloride.

A solution of 9.8 g of 4-chlorobenzohydroximoyl chloride in 300 ml of diethyl ether was chilled to 5°. To it was quickly added 10.4 g of triethylamine and, after 5 minutes, a solution of 6.1 g of methanesulfonyl chloride in 30 ml of diethyl ether was added dropwise during 30 minutes. The mixture was stirred for 1 hour at 0°–5°, followed by 1 hour at ambient temperature. The mixture was again cooled to 5°, then filtered, and the filter cake was washed with cold ether. The filtrate and washes were combined and the other evaporated under reduced pressure to leave a yellow oil. The oil was crystallized from a mixture of benzene and hexane to give 7.8 g of N-(methanesulfonyloxy)-4-chlorobenzimidoyl chloride, m.p. 80°–82°.

EXAMPLE III

N-(Methanesulfonyloxy)benzimidoyl chloride

Chlorine gas (7.9 g) was added to a cold (0° to −10°) solution of 12.1 g of benzaldoxime in 80 ml of chloroform. The mixture was stirred at −10° for half an hour and the solution of benzohydroximoyl chloride was used without further purification in an attempt to prepare the methanesulfonate as described in Example II-C. Work-up of the sulfonation mixture resulted in recovery of 9.4 g of unreacted benzohydroximoyl chloride, m.p. 50°–51°.

The 9.4 g of recovered benzohydroximoyl chloride was dissolved in 100 ml of anhydrous ether and the solution was cooled to −20°. To the cold solution was rapidly added 12.3 g of triethylamine. To this mixture was slowly added (during 45 minutes) a solution of 6.95 g of methanesulfonyl chloride in 50 ml of anhydrous ether. The mixture was stirred at −30° for 1 hour, then at ambient temperature for about 16 hours. The mixture was filtered and the filtrate was conconcentrated under reduced pressure to give a yellow solid. The solid was recrystallized from a benzene-hexane mixture to give 5.2 g of N-(methanesulfonyloxy)benzimidoyl chloride, m.p. 106°–108°.

EXAMPLE IV

N-(Methanesulfonyloxy)-3,4-dichlorobenzimidoyl chloride

A. Preparation of 3,4-dichlorobenzaldoxime.

A solution of 34.3 g of sodium hydroxide in 50 ml of water was slowly added to a solution prepared by mixing a solution of 47.5 g of hydroxylamine hydrochloride in 60 ml of water with a solution of 100 g of 3,4-dichlorobenzaldehyde in 300 ml of ethanol. The mixture was heated at reflux on a steam bath for half an hour, then stirred at ambient temperature for 16 hours. The separated solid was collected and the filtrate was poured into 600 ml of ice. Carbon dioxide was bubbled into the cold aqueous mixture for 30 minutes and the solid which separated was collected by filtration. The solids were triturated with hot methylene chloride and the methylene chloride removed to give 83.3 g of crude 3,4-dichlorobenzaldoxime which was used without further purification.

B. Preparation of 3,4-dichlorobenzohydroximoyl chloride.

A cold solution of 18.9 g of 3,4-dichlorobenzaldoxime in 150 ml of chloroform was treated with chlorine gas until no more chlorine was absorbed. The green mixture was stirred for 1 hour at 5°, then heated under reflux for 30 minutes, when the solid went into solution and the clear green solution changed to yellow. The solution was evaporated under reduced pressure to give a white solid, m.p. 104°–106°, which was used without further purification.

C. N-(Methanesulfonyloxy)-3,4-dichlorobenzimidoyl chloride.

The product from B was dissolved in 250 ml of cold (0°) anhydrous diethyl ether and to the solution was quickly added 15.2 g of triethylamine. The mixture was stirred at 0° for 5 minutes, and then to it was slowly added during 12 minutes a solution of 11.5 g of methanesulfonyl chloride in 25 ml of anhydrous ether. The mixture was stirred at 0°–5° for 1 hour, filtered and the filter cake washed with ether. The red filtrate and washes were combined and the ether evaporated under reduced pressure. The orange-brown residue was dissolved in chloroform, the insoluble solid removed by filtration and the chloroform removed under reduced pressure. The resultant residue was triturated with pentane. The pentane-insoluble solid was dissolved in chloroform and the solution was washed twice with 5% hydrochloric acid. The washed solution was dried over sodium sulfate and the chloroform was removed under reduced pressure. The residue was recrystallized twice from ethanol to give 8.3 g of N-(methanesulfonyloxy)-3,4-dichlorobenzimidoyl chloride, m.p. 73°–75°. The ir and nmr spectra were consistent with the assigned structure.

Analysis: Calc'd for $C_8H_6CL_3NO_3S$: C, 31.76; H, 2.00; N, 4.63; Cl, 35.15; S, 10.60. Found: C, 31.80; H, 1.80; N, 4.49; Cl, 34.81; S, 11.29.

EXAMPLE V

N-(Methanesulfonyloxy)-4-methoxybenzimidoyl chloride

A. Preparation of 4-methoxybenzaldoxime.

A solution of 68.1 g of 4-methoxybenzaldehyde in 300 ml of ethanol was prepared in a one-liter Erlenmeyer flask equipped with a magnetic stirrer. To this solution, 69.5 g of hydroxylamine hydrochloride dissolved in 70 ml of water was added in a single portion, and then 30 g of sodium hydroxide in 35 ml of water was added slowly during a period of 5 to 10 minutes. Water was added to the reaction mixture until it became cloudy, the diluted reaction mixture was heated for 30 minutes, allowed to cool, and the solid which formed was collected by filtration. The product was recrystallized from ethanol-water, then from ether-petroleum ether, to give 43.6 g of 4-methoxybenzaldoxime, m.p. 63.5°–66°. The ir spectrum was consistent with the assigned structure.

B. Preparation of 4-methoxybenzohydroximoyl chloride.

By the method of Example I-B, 43.6 g of methoxybenzaldoxime in 510 ml of ether was treated with 21.0 g of nitrosyl chloride. After removal of the ether, the product oil was triturated with benzene-hexane and crystallized from benzene-hexane. The filtrate from the crystallization was concentrated to about one-third of its original volume and placed in the refrigerator. The solid which formed and the first crop of crystals were combined and recrystallized from hexane-ether to give 13.2 g of 4-methoxybenzohydroximoyl chloride, m.p. 87.5°–89.5°. The ir spectrum was consistent with the assigned structure.

Analysis: Calc'd for $C_8H_8ClNO_2$: C, 51.77; H, 4.34; N, 7.55. Found: C, 52.11; H, 4.26; N, 7.26.

C. N-(Methanesulfonyloxy)-4-methoxybenzimidoyl chloride.

A solution of 13.2 g of 4-methoxybenzohydroximoyl chloride in 160 ml of ether ws prepared in a 250-ml, roundbottomed, three-necked flask equipped with a mechanical stirrer, thermometer, and drying tube and cooled in a methanol-ice bath to 0°–5°. Trimethylamine (10.1 g) was added dropwise during about 5 minutes to the solution at 0°–5°. The reaction mixture was stirred for 5 minutes, and 8.0 g of methanesulfonyl chloride in 16 ml of ether was added dropwise during 30 minutes. The final reaction mixture was stirred for 1 hour at 0°–5°, heated to boiling, cooled, and filtered. The precipitate was washed repeatedly with ether. The washings and filtrate were evaporated under reduced pressure. The product was recrystallized from ethanol to give 6.6 g of N-(methanesulfonyloxy)-4-methoxybenzimidoyl chloride, m.p. 105°–107.5°. The ir spectrum was consistent with the assigned structure.

Analysis: Calc'd for $C_9H_{10}ClCO_4S$: C, 41.00; H, 3.82; N, 5.31. Found: C, 40.94; H, 4.02; N, 5.46.

EXAMPLE VI

N-(Ethanesulfonyloxy)-4-methylbenzimidoyl chloride

A. Preparation of 4-methylbenzohydroximoyl chloride.

By the method of Example I-B, 132.7 g of 4-methylbenzaldoxine in 1400 ml of ether was treated with 70.7 g of nitrosyl chloride. After removal of the ether, the product was recrystallized twice from hexane to give 59.3 g of 4-methylbenzohydroximoyl chloride, m.p. 69°–71°.

B. N-(Ethanesulfonyloxy)-4-methylbenzimidoyl chloride.

A solution of 8.5 g of 4-methylbenzohydroximoyl chloride, 6.4 g of ethanesulfonyl chloride, and 150 ml of benzene was prepared in a 500-ml, three-necked flask equipped with a magnetic stirrer, thermometer, and drying tube. To this solution at room temperature, 7.6 g of triethylamine was added dropwise during a period of 14 minutes. At the end of the triethylamine addition, the temperature of the reaction mixture was 35°. The reaction mixture was stirred for 1 hour and then filtered, the filtrate was evaporated to an oil, and the oil was crystallized from ethanol to give 4.9 g of N-(ethanesulfonyloxy)-4-methylbenzimidoyl chloride, m.p. 55°–57.5°. The ir and nmr spectra were consistent with the assigned structure.

Analysis: Calc'd for $C_{10}H_{12}ClNO_3S$: C, 45.89; H, 4.62; N, 5.35. Found: C, 46.01; H, 4.70; N, 5.60.

EXAMPLE VII

N-(3-Chloropropanesulfonyloxy)-4-methylbenzimidoyl chloride

A. Preparation of 4-methylbenzohydroximoyl chloride.

By the method of Example I-B, 167.5 g of 4-methylbenzaldoxime in 1200 ml of ether was treated with 88.4 g of nitrosyl chloride. After removal of the ether, the product was recrystallized from hexane to give 62.5 g of 4-methylbenzohydroximoyl chloride, m.p. 70°–73°.

B.
N-(3-Chloropropanesulfonyloxy)-4-methylbenzimidoyl chloride.

To a solution of 8.5 g of 4-methylbenzohydroximoyl chloride and 8.8 g of 3-chloropropanesulfonyl chloride in 175 ml of benzene, 7.6 g of triethylamine was added dropwise during 8 minutes. The temperature of the reaction mixture rose to 35°. The reaction mixture was stirred for 1 hour and filtered, the filtrate was evaporated under reduced pressure, and the product was recrystallized twice from ethanol to give 8.4 g of N-(3-chloropropanesulfonyloxy)-4-methylbenzimidoyl chloride, m.p. 56°–58°. The ir spectrum was consistent with the assigned structure.

Analysis: Calc'd for $C_{11}H_{13}Cl_2NO_3S$: C, 42.59; H, 4.22; N, 4.52. Found: C, 42.76; H, 4.29; N, 4.74.

EXAMPLE VIII

N-(Methanesulfonyloxy)-4-ethoxybenzimidoyl chloride

A. Preparation of 4-ethoxybenzaldoxime.

A solution of 34.8 g of hydroxylamine hydrochloride in 50 ml of water was added in one portion to a solution of 37.5 g of 4-ethoxybenzaldehyde in 100 ml of ethanol in a 500-ml Erlenmeyer flask equipped with a magnetic stirrer. The reaction mixture was stirred for approximately 5 minutes, until clear. A room-temperature solution of 15.2 g of sodium hydroxide in 20 ml of water was added in several portions during 15 minutes. The reaction mixture was stirred for 5 minutes and then heated to boiling. After the cloudy reaction mixture had cooled to room temperature, water was added and product separated from solution as an oil. The mixture was extracted four times with 50-ml portions of chloroform. The chloroform extracts were combined, washed twice with 75-ml portions of saturated aqueous sodium chloride solution and dried over sodium sulfate. The dry chloroform solution was filtered, the filtrate was evaporated, and the residue crystallized with a slight amount of cooling. The crude solid was recrystallized from cyclohexane to give 35.4 g of 4-ethoxybenzaldoxime, m.p. 81°–86°. The ir spectrum was consistent with the assigned structure.

B. Preparation of 4-ethoxybenzohydroximoyl chloride.

A solution of 35.5 g of 4-ethoxybenzaldoxime in 350 ml of ether was prepared in a one-liter flask. From a pressure bottle, 16.4 g of nitrosyl chloride was run into a cold flask and allowed to distill slowly, thence into the reaction mixture at 0° ± 5°. The reaction mixture was stirred for 2 hours in an ice bath, the ether was evaporated, the remaining oil was triturated with hexane, the resulting mixture was filtered, and the filter cake was recrystallized twice from cyclohexane to give 13.5 g of 4-ethoxybenzohydroximoyl chloride, m.p. 87°–89°. The ir spectrum was consistent with the assigned structure.

Analysis: Calc'd for $C_9H_{10}ClNO_2$: C, 54.15; H, 5.05; N, 7.02. Found: C, 54.05; H, 5.15; N, 6.71.

C. N-(Methanesulfonyloxy)-4-ethoxybenzimidoyl chloride.

In a 250-ml, three-necked, round-bottomed flask equipped with a thermometer, drying tube, and magnetic stirrer, 10 g of 4-ethoxybenzohydroximoyl chloride was dissolved in 200 ml of benzene. To this, 5.7 g of methanesulfonyl chloride was added in one portion, followed by dropwise addition of 7.6 g of triethylamine during 15 minutes. During the addition, the exothermic reaction increased the temperature to 40°. The reaction mixture was stirred for one hour and filtered. The filter cake was washed with benzene, the filtrate was evaporated to a solid which was recrystallized twice from ethanol to give 8.1 g of N-(methanesulfonyloxy)-4-ethoxybenzimidoyl chloride, m.p. 93°–95.5°. The ir spectrum was consistent with the assigned structure.

Analysis: Calc'd for $C_{10}H_{12}ClNO_4S$: C, 43.25; H, 4.36; N, 5.04. Found: C, 43.49; H, 4.26; N, 4.86.

EXAMPLE IX

N-(Ethanesulfonyloxy)-4-fluorobenzimidoyl chloride

A. Preparation of 4-fluorobenzohydroximoyl chloride.

A solution of 25 g of 4-fluorobenzaldoxime in 200 ml of chloroform was cooled to 0° to −10°. From a pressure bottle, 14.2 g of chlorine was run into a flask cooled by dry ice-acetone and allowed to distill into the aldoxime solution, the solution being maintained at 0° ± 5°. The reaction mixture was stirred for one hour in an ice bath while nitrogen was bubbled through the solution. The chloroform was evaporated to leave an oil to which hexane was added quickly. The solid which separated was recrystallized from hexane to give 15.0 g of 4-fluorobenzohydroximoyl chloride, m.p. 74.5°–75°. The ir spectrum was consistent with the assigned structure.

Analysis: Calc'd for $C_7H_5ClFNO$: C, 48.44; H, 2.90; N, 8.07. Found: C, 48.57; H, 3.05; N, 7.78.

B. N-(Ethanesulfonyloxy)-4-fluorobenzimidoyl chloride.

Six grams of 4-fluorobenzohydroximoyl chloride was dissolved in 200 ml of benzene in a 250-ml, three-necked, round-bottomed flask equipped with a magnetic stirrer, thermometer, dropping funnel, and drying tube. A 4.5-g portion of ethanesulfonyl chloride was added; then 5.1 g of triethylamine was added dropwise during 15 minutes. The temperature of the reaction mixture was 40° after the addition of the triethylamine. The reaction mixture was stirred for 45 minutes and filtered. The filter cake was washed with benzene, and the filtrate plus washes were combined and concentrated to give an oil. The oil was dissolved in ethanol and the solution was placed in a refrigerator. Solid was frozen out in dry ice-acetone and recrystallized from ethanol in a low-temperature recrystallization apparatus to give 5.6 g of N-(ethanesulfonyloxy)-4-fluorobenzimidoyl chloride, m.p. 39°–41.5°. The ir spectrum was consistent with the assigned structure.

Analysis: Calc'd for $C_9H_9ClFNO_3S$: C, 40.49; H, 3.41; N, 5.27. Found: C, 40.89; H, 3.64; N, 5.19.

EXAMPLE X

N-(Propanesulfonyloxy)-4-methylbenzimidoyl chloride

Eight and one-half grams of 4-methylbenzohydroximoyl chloride, prepared as in Example VI-A, was treated with 7.1 g of propanesulfonyl chloride in the same manner as described in Example VI-B. Recrystallization of the oil from ethanol gave 8.1 g of N-(propanesulfonyloxy)-4-methylbenzimidoyl chloride, m.p. 57.5°–60.5°. The ir spectrum was consistent with the assigned structure.

Analysis: Calc'd for $C_{11}H_{14}ClNO_3S$: C, 47.91; H, 5.12; N, 5.08. Found: C, 48.55; H, 5.35; N, 5.29.

EXAMPLE XI

N-(Methanesulfonyloxy)-4-methylbenzimidoyl bromide

A. Preparation of 4-methylbenzohydroximoyl chloride.

By the method of Example I-B, 67.6 g of 4-methylbenzaldoxime in 600 ml of ether was treated with 39.3 g of nitrosyl chloride. After removal of the ether, the product was recrystallized twice from hexane to give 30 g of 4-methylbenzohydroximoyl chloride, m.p. 70°–73°.

B. N-(Methanesulfonyloxy)-4-methylbenzimidoyl bromide.

A solution of 8.5 g of 4-methylbenzohydroximoyl chloride in 150 ml of diethyl ether was cooled to 0°–10° and to it was added dropwise 11.1 g of triethylamine. The mixture was stirred for 2 hours at 0°–10°. The mixture was filtered, and to the filtrate was added in one portion without cooling 9.1 g of triethylamine hydrobromide. To this mixture was added during ten minutes 8.0 g of methanesulfonyl bromide. The temperature of the mixture increased to 35°. The mixture was stirred for 35 minutes and filtered. The filtrate was concentrated to leave an oil which was recrystallized twice from ethanol to give crystals, m.p. 82.5°–91.5°. Recrystallization from cyclohexane gave N-(methanesulfonyloxy)-4-methylbenzimidoyl bromide, m.p. 95°–97.5°. The ir spectrum was consistent with the assigned structure.

Analysis: Calc'd for $C_9H_{10}BrNO_3S$: C, 37.00; H, 3.45; N, 4.79. Found: C, 37.30; H, 3.55; N, 4.76.

EXAMPLE XII

N-(Methanesulfonyloxy)-4-isopropylbenzimidoyl chloride

A. Preparation of 4-isopropylbenzohydroximoyl chloride.

A solution of 5.4 g of tert-butyl hypochlorite in 25 ml of carbon tetrachloride was added dropwise during 15 minutes into a solution of 6.8 g of 4-isopropylbenzaldoxime (m.p. 61°–63°, prepared in the manner described in Example II) in 50 ml of carbon tetrachloride while the temperature was maintained at 15°–23°. The green mixture was stirred for 15 minutes, then concentrated. The oil was crystallized from hexane to give 6 g of 4-isopropylbenzohydroximoyl chloride.

B. N-(Methanesulfonyloxy)-4-isopropylbenzimidoyl chloride.

Into a solution of 6.7 g of 4-isopropylbenzohydroximoyl chloride in 175 ml of benzene was added in one portion 5.2 g of triethylamine. To this solution was added dropwise during 15 minutes (mildly exothermic reaction) 4.0 g of methanesulfonyl chloride. The mixture was stirred for 30 minutes and filtered. The filtrate was concentrated and the residue recrystallized twice from ethanol to give 8.1 g of N-(methanesulfonyloxy)-4-isopropylbenzimidoyl chloride, m.p. 79.5°–82°. The ir spectrum was consistent with the assigned structure.

Analysis: Calc'd for $C_{11}H_{14}ClNO_3S$: C, 47.91; H, 5.12; N, 5.08. Found: C, 48.29; H, 5.16; N, 5.06.

EXAMPLE XIII

N-(Methanesulfonyloxy)-4-ethylbenzimidoyl chloride

A solution of 20 g of 4-ethylbenzaldoxime in 125 ml of carbon tetrachloride was treated as described in Example XII-A with 14.1 g of tert-butyl hypochlorite in 40 ml of carbon tetrachloride to give 9.3 g of oil which was used without further purification.

The oil was dissolved in 200 ml of benzene and to the solution was added 7.6 g of triethylamine in one portion, followed by 5.7 g of methanesulfonyl chloride which was added dropwise. The mixture was treated as described in Example XII, except that recrystallization was from hexane, to give 5.2 g of N-(methanesulfonyloxy)-4-ethylbenzimidoyl chloride, m.p. 50°–52°.

Analysis: Calc'd for $C_{10}H_{12}ClNO_3S$: C, 45.89; H, 4.62; N, 5.35. Found: C, 45.64; H, 4.80; N, 5.24.

In similar manner were prepared:

| | | |
|---|---|---|
| Example XIV - | N-(Methanesulfonyloxy) chloride, | -3-methylbenzimidoyl m.p. 66–68° |
| Example XV - | N-(Butanesulfonyloxy) chloride, | -4-methylbenzimidoyl m.p. 35.5–37° |
| Example XVI - | N-(Methanesulfonyloxy) chloride, | -4-bromobenzimidoyl m.p. 88–90.5° |
| Example XVII - | N-(Methanesulfonyloxy) chloride, | -4-butoxybenzimidoyl m.p. 51–53° |
| Example XVIII - | N-(Methanesulfonyloxy) benzimidoyl chloride, | -3,4-methylenedioxy- m.p. 87–88° |
| Example XIX - | N-(Methanesulfonyloxy) chloride, | -3-nitrobenzimidoyl m.p. 99.5–101.5° |
| Example XX - | N-(Methanesulfonyloxy) chloride, | -4-nitrobenzimidoyl m.p. 154–156° |
| Example XXI - | N-(Methanesulfonyloxy) chloride, | -3-chlorobenzimidoyl m.p. 64–67° |
| Example XXII - | N-(Methanesulfonyloxy) chloride, | -4-fluorobenzimidoyl m.p. 78.5–80.5° |

-continued

| | | |
|---|---|---|
| Example XXIII - | N-(2-Propenesulfonyloxy) chloride, | -4-methylbenzimidoyl m.p. 76-77° |
| Example XXIV - | N-(Ethanesulfonyloxy) chloride, | -4-isopropylbenzimidoyl m.p. 51-52.5° |
| Example XXV - | N-(Methanesulfonyloxy) chloride, | -4-tert-butylbenzimidoyl m.p. 69-71.5° |
| Example XXVI - | N-(Methanesulfonyloxy) chloride, | -2-chlorobenzimidoyl m.p. 54.5-56.5° |

EXAMPLE XXVII

Antifungal Tests in vitro

For mycelial growth tests, the test chemical was dissolved or suspended in analytically pure acetone. Appropriate dilution was made in acetone to give the desired concentrations. An aliquot of the prepared dilution was added to tubes of 20 ml of sterile, melted potato-dextrose agar cooled to 45°. The tubes were shaken to insure thorough mixing and the treated agar was poured into petri dishes. The compounds were tested at 2.5, 5, or 10 ppm w/v. When the agar had solidified, it was point-inoculated with a 4 mm block of agar permeated with the test fungus. The inoculated agar was incubated at 25° in intermittent low-intensity light (12 hours on and 12 hours off) for up to six days (depending on the rate of growth of an untreated colony). The diameter of each colony was measured and compared to the diameter of a colony grown in untreated agar. The result with an untreated control in each case was designated 0% inhibition, and control of the test organism was reported as precent inhibition of growth. The results recorded in Table 1 illustrate that test compounds are specific in their inhibition and can yield variable results.

In tests of spore germination in vitro, the active ingredients of the invention were found to be of limited activity or essentially inactive in inhibiting germination.

Table 1

Agar Growth Test in vitro

| Compound of Example | ppm | Percent Inhibition of Test Organism Growth | | | | | | | | |
|---|---|---|---|---|---|---|---|---|---|---|
| | | V | P | Fs | R | Py | H | Sf | A | F |
| I | 2.5 | 20 | 100 | 58 | 38 | 22 | 100 | 0 | | |
| | 5 | | 90 | | | | 92.5 | 86.7 | 89.3 | 47.9 |
| | 10 | | 100 | | | | 100 | 100 | 100 | 23.5 |
| IV | 5 | (45.5 | 50 | | | | 42.9 | 66.7 | | 44.7 |
| | | (12.5 | 33.3 | | | | 37.5 | 60 | | 33.3 |
| V | 5 | | 10 | | | | 32 | 23 | 16 | 18 |
| VI | 2.5 | 100 | | 10 | | 100 | 80 | | | |
| | 5 | | 89 | 27 | 66 | | 100 | 62 | 46 | 30 |
| VII | 2.5 | | 53 | | | 0 | 60 | 0 | 0 | 30 |
| VIII | 5 | 5 | 13 | 17 | 0 | 0 | 29 | 0 | 5 | 15 |
| IX | 5 | 0 | 25 | 0 | 35 | 0 | 20 | 23 | 0 | 80 |
| X | 5 | 21 | 75 | 9 | 48 | 33 | 0 | 70 | 24 | 45 |
| | 10 | | 100 | | 35 | | 100 | 64 | 100 | |
| XI | 2.5 | 12.5 | 83 | 9 | 25 | 100 | 100 | 77 | 46 | 36.8 |
| | 5 | 0 | 100 | 0 | 85 | 100 | 100 | 95 | 26 | 69 |
| XIV | 2.5 | | 88 | | 3 | | 60 | 83 | 70 | 10 |
| | 5 | 13 | 100 | 37 | 56 | 20 | 100 | 83 | 57 | 60 |
| XV | 2.5 | 0 | 100 | 23 | 4 | 0 | 68.5 | 33 | 29 | 21 |
| | 5 | 0 | 92 | 0 | 51 | 0 | 63 | 45 | 21 | 38 |
| XVI | 2.5 | | | 25 | 14 | 11 | 75 | | 37.5 | 40 |
| | 5 | 11 | 19 | 42 | 48 | 100 | 57 | 14 | 24 | 19 |
| XVII | 5 | 0 | 32 | 21 | 20 | 0 | 0 | 0 | 0 | 62 |
| XVIII | 5 | (9.1 | 50 | | | | 42.9 | 33.3 | | 21.3 |
| | | (6.3 | 33.3 | | | | 33.3 | 20 | | 4.8 |
| | 10 | | 22.2 | | | | 31.3 | 25 | 40 | 0 |

Test organisms used in these tests were as follows:
V   Verticillium albo-atrum      Cotton defoliation wilt
P   Piricularia oryzae           Rice blast
Fs  Fusarium solani              Root rot of bean
R   Rhizoctonia solani           Root rot
Py  Pythium ultimum              Root rot
H   Helminthosporium oryzae      Brown spot of rice
Sf  Sclerotinia fructicola       Brown rot
A   Alternaria solani            Early blight
F   Fusarium oxysporum           Wilt of tomato

EXAMPLE XXVIII

Foliar Protection Against Fungal Disease Organisms

Active ingredients were formulated for tests as 25% wettable powders comprising 72% of attapulgite clay, 1.5% of a sodium lignosulfonate and 1.5% of sodium alkylnaphthalenesulfonate in addition to 25% of test compound. A 25% wettable powder was suspended in sufficient tap water to provide 150 ppm of active ingredient, and the aqueous suspension was sprayed onto the host plant and allowed to dry.

The suspensions of active ingredient were sprayed onto the host plants by two stationary atomizing nozzles operating at 20 lbs pressure. Aqueous bacterial suspensions containing 5% of carborundum powder were applied to the host plants by spraying at 40 lbs pressure. Those fungal disease organisms which were sprayed onto the plants were applied at 20 lbs pressure. In other cases, fungal disease organisms were wiped on, dusted on, or applied by an artificial spore shower.

The spraying period was timed with a stop watch. The nozzle delivery rate was determined prior to each test and the spraying time was adjusted accordingly. During the spraying, the pots were rotated on a compound turntable which accommodates eight plants at a time and which rotates each pot one-quarter turn per revolution of the table. The suspension being sprayed was constantly stirred by a magnetic stirrer. The spray lines and nozzles were thoroughly cleaned with an organic solvent, hot soapy water, and finally cold tap water, before being used to apply the pathogen.

Plants which were not treated with test chemical were included in each test. Percent disease control of the test chemicals was estimated by comparing the degree of infection of treated plants with the degree of infection of untreated plants. Plants were treated with standard commercial compounds where available as a basis for comparison of the efficacy of the test chemicals.

Procedures used in the individual screening tests are set forth below, and results are summarized in Table 2.

A. Control of late blight.

Four-week-old tomato plants (*Lycopersicon esculentum* var. Heinz 1350) were treated with test chemical as described and allowed to dry. Within 24 hours after the host plants had been sprayed with chemical, they were sprayed with an aqueous suspension of the zoospores of *Phytophthora infestans* (late blight) for 1 minute. The host plants were incubated in the humidity chamber and maintained at 20° and 100% relative humidity for 3 days. The percent control of disease was recorded. The efficacy of test chemicals was compared to that of a mixture of 5.2 parts by weight (83.9%) of ammoniates of [ethylenebis(dithiocarbamato)]-zinc with 1 part by weight (16.1%) of [ethylenebis-(dithiocarbamic acid]bimolecular and trimolecular cyclic anhydrosulfides and disulfides, for which the registered trademark is Polyram.

B. Control of bean rust.

Pinto bean plants (*Phaseolus vulgaris* var. Pinto) having two fully expanded primary leaves were sprayed with test chemical. Within 24 hours, a 2% spore powder consisting of uredospores of *Uromyces phaseoli* var. *typica* (causal organism of bean rust) admixed with talc was dusted onto the leaves of the host plants. The host plants were incubated in the humidity chamber at 20° and 100% relative humidity for 24 hours and then transferred to the greenhouse until disease symptoms developed, 4 to 6 days later. The percent control of bean rust was recorded. Polyram was included for comparison.

C. Control of bean powdery mildew.

Bush bean plants (*Phaseolus vulgaris* var. Bountiful) were sprayed with test chemical. Within 24 hours, the host plants were infected with *Erysiphe polygoni* (causal organism of bean powdery mildew) by shaking diseased leaves over them. The host plants were incubated in the greenhouse for approximately a week, after which the percent control of bean powdery mildew was recorded. Karathane was included for comparison.

D. Control of bacterial spot.

Four-week-old tomato plants (*Lycopersicon esculentum* var. Heinz 1350) were sprayed with test chemical. Within 24 hours, the chemically treated plants were sprayed at 40 lbs pressure with an aqueous suspension of *Xanthomonas vesicatoria* (causal organism of bacterial spot) containing 5% of carborundum powder. The host plants were incubated in the greenhouse for 3 to 5 days, after which the percent control of bacterial spot was recorded. Streptomycin sulfate was included for comparison.

E. Control of rice blast.

Stands of rice (*Oryza sativa* var. Bluebonnet), consisting of 25 plants at the two- to three-leaf stage per pot, were sprayed with the test chemical. Within 24 hours, the plants were sprayed with an aqueous suspension of *Piricularia oryzae* (International Race Group ID, Race 5) (causal organism of rice blast) containing 5 drops of 8% Triton X-100 per 750 ml of water. The host plants were incubated in the humidity chamber at 22° and 100% relative humidity for 36 hours, then transferred to the greenhouse until disease symptoms appeared, in approximately 4 days. The percent control of rice blast was recorded. Blasticidin-S and Kasugamycin were included for comparison.

F. Control of angular leaf spot.

Cucumber plants (*Cucumis sativus* L. var. Straight Eight) with the second true leaf emerging were sprayed with test chemical. Within 24 hours, the chemically treated plants were sprayed with an aqueous suspension of *Pseudomonas lachrymans* (causal organism of angular leaf spot) containing 5% of carborundum powder. The host plants were incubated in the greenhouse from 4 to 6 days, after which the percent control of angular leaf spot was recorded. Streptomycin sulfate was included for comparison.

Table 2

| Compound of Example | ppm | Pi | Up | Ep | Xv | P | Pl |
|---|---|---|---|---|---|---|---|
| I | 150 | 96 | 100 | 0 | 0 | 95 | |
| II | 150 | 0 | 0 | 0 | 0 | 75 | |
| III | 150 | 0 | 98 | 0 | 0 | 0 | |
| IV | 150 | 95 | 100 | 0 | 0 | 100 | |
| V | 150 | 90 | 100 | 0 | 0 | 95 | |
| VI | 150 | 98 | 100 | 80 | 0 | 98 | |
| VII | 150 | 0 | 100* | 100 | 0 | 96 | 50 |
| VIII | 150 | 98 | 100 | 100 | 0 | 100 | 0 |
| IX | 150 | 0 | 100 | 0 | 90 | 0 | 0 |
| X | 150 | 95 | 100 | 0 | 0 | 90 | 0 |
| XI | 150 | 98 | 100 | 0 | 0 | 100 | 0 |
| XIV | 150 | 95 | 100 | 0 | 0 | 98 | |
| XV | 150 | 0 | 100 | 100 | 0 | 100 | 0 |
| XVI | 150 | 95 | 100 | 0 | 0 | 100 | 0 |
| XVII | 150 | 85 | 96 | 95 | 0 | 0 | 0 |
| XVIII | 150 | 0 | 99 | 0 | 0 | 95 | |
| XIX | 150 | 0 | 100 | 0 | 0 | 95 | |
| XX | 150 | 0 | 75 | 0 | 0 | 85 | |
| XXI | 150 | 0 | 100 | 0 | 0 | 100 | |
| Comparison Compounds | | | | | | | |
| Polyram | 150 | 97 | 99 | | | | |
| Karathane | 150 | | | 100 | | | |
| Streptomycin | 600 | | | | 70 | | 92 |
| Kasugamycin | 40 | | | | | 95 | |
| Blasticidin-S | 20 | | | | | 95 | |

*Slight chemical injury

Test organisms used were as follows:
Pi  *Phytophthora infestans*   Late blight
Up  *Uromyces phaseoli* var. *typica*   Bean rust
Ep  *Erysiphe polygoni*   Bean powdery mildew
Xv  *Xanthomonas vesicatoria*   Bacterial spot
P   *Piricularia oryzae*   Rice blast
Pl  *Pseudomonas lachrymans*   Angular leaf spot

EXAMPLE XXIX

Multiple-Level Testing Against Fungal Disease Organisms

Following the same procedures used in Example XXVIII, evaluations of active ingredients at multiple levels of application were carried out on the same pathogen-host systems and on additional pathogen-host pairs.

Activity against late blight on tomatoes, bean rust and rice blast was confirmed as Tables 3, 4 and 5 illustrate. In addition, activity against *Helminthosporium oryzae* (causal agent of brown spot of rice) is shown by the results in Table 6; against *Venturia inaequalis* (causal agent of apple scab) is shown by the results in Table 7; and against *Cercospora beticola* (causal agent of leaf spot of sugar beet) is shown by the results in Table 8. Details of the evaluation methods used for brown spot, apple scab, and leaf spot are set forth below.

G. Control of brown spot of rice.

Stands of rice (*Oryza sativa* var. Bluebonnet), consisting of 25 plants/pot at the two- to three-leaf stage, were sprayed with a test chemical. Within 24 hours, the plants were sprayed with an aqueous suspension of *Helminthosporium oryzae* (causal agent of brown spot of rice) containing 5 drops of 8% Triton X-100 and 750 ml of water. The host plants were incubated in a humidity chamber at 22° and 100% relative humidity for 24 hours, then transferred to the greenhouse until disease symptoms appeared (approximately 4 days). The percent control of brown spot was recorded. Polyram was included for comparison.

H. Control of apple scab.

Apple seedlings (from germinated seeds of McIntosh apples) with six to eight fully formed leaves were sprayed to run-off with test chemical at a rate of 600 ppm of active ingredient. Within 24 hours, the chemically treated seedlings were sprayed with conidia of *Venturia inaequalis* (causal organism of apple scab). Conidia were obtained by washing infected leaves. The inoculated seedlings were incubated in the humidity chamber at 21° and 100% relative humidity for 1 day, then incubated in the greenhouse until disease symptoms appeared (usually 2 to 3 weeks). The percent control of apple scab was recorded. The results are summarized in Table 7.

I. Control of leaf spot of sugar beet.

Three-week-old sugar beet plants (*Beta vulgaris* var. A436-67R) at the four-leaf stage were sprayed with test chemical. Within 24 hours, the chemically treated plants were sprayed with an aqueous suspension of conidia of *Cercospora beticola* (causal organism of leaf spot of sugar beet). The inoculated plants were incubated in the humidity chamber at 22° and 100% relative humidity for 2 days and then transferred to the greenhouse until disease symptoms developed (about 2 weeks). The percent control of leaf spot of sugar beet was recorded. The results are summarized in Table 8.

Table 3

| Foliar Protection Against Late Blight on Tomato | | | | |
|---|---|---|---|---|
| Compound | Percent Disease Control at ppm of Compound | | | |
| of Example | 300 | 150 | 75 | 38 | 19 |
| I | 94 | 74 | 94 | | |
| | | | | 38 | 14 |
| IV | 98 | | 96 | | 33 |
| | 0 | 0 | 0 | | |
| V | 100* | 97* | 98* | | |
| VI | 95 | 95 | 69 | | |
| VII | | 44 | | | 2 |
| VIII | | 98 | | 97 | |
| X | 92 | 86 | 0 | | |
| XI | | 18 | 92 | | |
| XIV | 96 | 92 | 92 | | |
| XV | | 71 | 61 | | |
| XVI | | 40 | 5 | | |
| XVII | | 1 | | 1 | |

Table 3-continued

| Foliar Protection Against Late Blight on Tomato | | | | |
|---|---|---|---|---|
| Compound | Percent Disease Control at ppm of Compound | | | |
| of Example | 300 | 150 | 75 | 38 | 19 |
| Polyram | 99 | 98 | 94 | 82 | 94 |

*Slight chemical injury

Table 4

| Foliar Protection Against Bean Rust | | | | |
|---|---|---|---|---|
| Compound | Percent Disease Control at ppm of Compound | | | |
| of Example | 300 | 150 | 75 | 38 | 19 |
| I | 100 | | 50 | | 0 |
| | | 100 | | 96 | |
| II | | 97 | | 93 | |
| III | 95* | | | | 0 |
| | | 100 | | 100 | |
| IV | 100 | 100 | 97 | | |
| | 98 | | 92 | | 75 |
| | | 96 | | 54 | |
| V | 100 | | 100 | | |
| VI | | 100 | | 100 | |
| VII | | 100 | | 100 | |
| VIII | | 100 | | 100 | |
| IX | 100 | | 98 | | 85 |
| XIX | | 100 | | 93 | |
| Polyram | 100 | 100 | 99 | 100 | 98 |

*Moderate chemical injury

Table 5

| Foliar Protection Against Rice Blast | | | |
|---|---|---|---|
| Compound | Percent Disease Control at ppm of Compound | | |
| of Example | 300 | 150 | 75 | 38 | 19 |
| I | | 97 | | 93 | |
| | 85 | 85 | 80 | | |
| II | | 97 | | 13 | |
| III | | 100 | | 63 | |
| IV | | 100 | | 94 | |
| VI | | 100 | | 98 | |
| VII* | | 100 | | 98 | |
| | | 100 | | 95 | |
| VIII* | | 100 | | 95 | |
| | | 98 | | 97 | |
| X | | 100 | | 100 | |
| XI | | 100 | | 98 | |
| XIV | | 100 | | 95 | |
| XV | | 98 | | 87 | |
| XVI* | | 100 | | 98 | |
| XVII* | | 100 | | 92 | |
| XVIII | | 95 | 80 | | 25 |
| XX | | 78 | | 13 | |
| XXI | 100 | 99 | 86 | | |
| Kasugamycin | | 95 | | 95 | |

*Disease control on new growth was 93–98% at 150 ppm, 69–93% at 38 ppm.

Table 6

| Foliar Protection Against Brown Spot of Rice | | | |
|---|---|---|---|
| Compound | Percent Disease Control at ppm of Compound | | |
| | Original Growth | | New Growth | |
| of Example | 150 | 38 | 150 | 38 |
| I | 90 | 36 | | |
| II | 100 | 25 | | |
| III | 0 | 0 | | |
| IV | 93 | 0 | | |
| V | 90 | 50 | | |
| VI | 98 | 92 | | |
| VII | 100 | 98 | 98 | 64 |
| VIII | 100 | 97 | 98 | 50 |
| X | 90 | 35 | | |
| XI | 50 | 77 | | |
| XIV | 76 | 76 | | |
| XV | 100 | 89 | | |
| XVI | 100 | 98 | 92 | 71 |
| XVII | 100 | 95 | 94 | 57 |
| XIX | 90 | 50 | | |

Table 6-continued

Foliar Protection Against Brown Spot of Rice

| Compound of Example | Percent Disease Control at ppm of Compound | | | |
|---|---|---|---|---|
| | Original Growth | | New Growth | |
| | 150 | 38 | 150 | 38 |
| XX | 50 | 0 | | |
| XXI | 61 | 8 | | |
| Polyram | 98 | 96 | 97 | 95 |

Table 7

Foliar Protection Against Apple Scab

| Compound of Example | Percent Disease Control at 600 ppm of Compound |
|---|---|
| I | 100 |
| VI | 100 |
| X | 67 |
| XIV | 94 |
| Captan | 100 |

Table 8

Foliar Protection Against Leaf Spot of Sugar Beet

| Compound of Example | Percent Disease Control at ppm of Compound | |
|---|---|---|
| | 150 | 38 |
| I | 97 | 86 |
| X | 82 | 0 |

The ineffectiveness of the active ingredients against bacterial spot on tomato and angular leaf spot on cucumber, and their relative inactivity against bean powdery mildew on bush beans, were confirmed in the multiple-level evaluations. Ineffectiveness against *Erysiphe cichoracearum* (causal organism of cucumber powdery mildew) and against *Helminthosporium maydis* race T (causal agent of southern corn leaf blight) was also observed. Details of this group of evaluations and the negative results they yielded are not recorded.

EXAMPLE XXX

Residual Foliar, Systemic, and Soil Incorporation Tests of Fungicidal Efficacy

Tests of residual foliar activity utilized the procedures employed for foliar protectant tests, except that the host plants were inoculated with pathogenic organisms 3 to 5 days or 7 days after being treated with chemical. The compound of Example I showed 100% control of bean rust 6 days after application at a rate of 300 ppm. The compound of Example XIV, applied at 300 ppm, showed 100% control of bean rust introduced 3 to 5 days after chemical treatment, but no residual activity against late blight introduced 3 to 5 days after chemical treatment.

At the concentrations which were tested, the active ingredients of the compositions of the present invention showed limited downward systemic activity against Fusarium root rot, and showed no evidence of upward systemic activity against bean rust. Protection of seeds against root rot by incorporating test compounds in the soil was provided by some of the active ingredients of the invention.

EXAMPLE XXXI

Tests of Miticidal Activity

Compounds of the present invention in which Y is hydrogen, halogen or alkyl of 1 to 4 carbon atoms; Z is hydrogen; X is chlorine or bromine; and R is alkyl of 1 to 4 carbon atoms, which may carry a halogen, or allyl, show outstanding activity as miticides and as mite ovicides.

Preferred as miticides are compounds in which Y is alkyl of 1 to 4 carbon atoms or fluorine; Z is hydrogen; X is chlorine; and R is alkyl of 1 to 4 carbon atoms. Especially preferred as miticides are compounds in which Y is 4-ethyl, 4-isopropyl or fluorine; Z is hydrogen; X is chlorine; and R is methyl, ethyl or propyl.

A. Against adult mites.

A small section of a highly infested pinto bean (*Phaseolus vulgaris*) plant leaf containing 50 to 75 adult female two-spotted mites (*Tetranychus urticae*) was placed in an inverted position on the upper surface of each of the leaves of a growing bean seedling. When migration to the leaves of the growing plant was complete (2 to 4 hours), the seedling leaves were briefly immersed in an aqueous-acetone (10% acetone) solution containing the N-(alkanesulfonyloxy)benzimidoly halide at the desired cencentration. The infested and treated plants were maintained at 26.6° and 50% relative humidity for 48 hours, after which time counts were made of dead and living mites. Results are summarized in Table 9.

B. Against mite eggs.

Leaves of growing pinto bean seedlings were infested with adult female two-spotted mites as described above. Two to 4 hours later, when the eggs had been deposited, the adult females were killed by treatment of the leaves with an aqueous solution containing 936 ppm of tetraethyl pyrophosphate (TEPP), a known miticide having essentially no effect on mite eggs. After the plant leaves had dried, they were dipped in an aqueous-acetone solution of the N-(alkanesulfonyloxy)benzimidoyl chloride as described above. The plants were maintained at 26.6° and 50% relative humidity for 7 days, after which time a count of unhatched eggs and dead and living immature mites was made. Results are summarized in Table 9.

Some of the compounds of the present invention have shown activity as nematicides. For example, the compounds of Examples I and X gave complete control of root knot nematodes (*Meloidogyne incognita*) when incorporated into infested soil at a concentration of 25 ppm relative to the weight of soil.

The effective compositions of this invention are obtained when N-(sulfonyloxy)benzimidoyl halides are formulated with any of the relatively inert adjuvants and carriers

Table 9

Testing Against Mites and Mite Ova

| Compound of Example | ppm | Percent Kill after exposure of | |
|---|---|---|---|
| | | 48 hrs. Mites | 7 days Eggs |
| I | 625 | 95[1] | 93 |
| | 312 | 97[1] | 91 |
| II | 625 | | 68 |
| III | 625 | | 98 |
| VI | 625 | 100[2] | |
| | 312 | 100[2] | 100[2,3] |
| | 156 | 100[2] | 100[2,3] |
| VII | 625 | 55[1] | 100 |
| | 312 | 33[1] | 100 |

Table 9-continued

Testing Against Mites and Mite Ova

| Compound of Example | ppm | 48 hrs. Mites | Percent Kill after exposure of 7 days Eggs |
|---|---|---|---|
| X | 625 | 100[2] | |
| | 312 | 99[2] | 100 |
| | 156 | 99[2] | 78 |
| XII | 312 | 100 | 99 |
| | 156 | 98[2] | 100 |
| XIII | 312 | 100[3] | 100[3] |
| | 156 | 100[2,3] | 100[3] |
| XIV | 625 | 99[2] | 10 |
| | 312 | 97[1] | 2 |
| XV | 625 | 100[2] | 8[3] |
| | 312 | 100[2] | 1 |
| XXII | 625 | 100[3] | 75 |
| | 312 | 100[3] | 5 |
| XXIII | 312 | 21 | |
| | 156 | 5 | 96 |
| | 39 | | 87 |
| XXIV | 625 | 100[4] | |
| | 156 | 88[4] | 11 |
| XXV | 625 | 100[4] | |
| | 156 | 97[4] | 2 |
| XXVI | 625 | 96[1] | 97 |

[1] Partial kill of immature mites
[2] All immature mites killed
[3] Phytotoxicity observed
[4] 72-hour exposure (instead of 48).

normally employed for facilitating the dispersion of active ingredients for agricultural applications, recognizing the fact that the formulation and mode of application of a toxicant may affect the activity of the material in a given application. If the formulation permits even distribution of the active ingredients and provides contact with the area to be treated, the precise nature of the formulation is not critical. Thus the N-(sulfonyloxy)benzimidoyl halides may be formulated as wettable powders, as dusts, as emulsifiable concentrates, as solutions, or as any of several other known types of formulations depending on the desired mode of application. These formulations may contain as little as 0.5% to as much as 95% or more by weight of active ingredient.

Wettable powders are in the form of finely divided particles which disperse readily in water or other dispersant. The wettable powder is ultimately applied either as a dry powder or as a suspension in water or other liquid. Typical carriers for wettable powders include fuller's earth, kaolin clays, silicas or other readily wet organic or inorganic diluents. Wettable powders normally are prepared to contain about 5 to 95% of active ingredient, depending on the absorbency of the carrier, and usually also contain a small amount of a wetting or dispersing agent. For example, a useful wettable powder formulation contains 25.0 parts of N-(methanesulfonyloxy)-4-methylbenzimidoyl chloride, 72.0 parts of attapulgite clay, and 1.5 parts of sodium lignosulfonate and 1.5 parts of sodium alkylnaphthalenesulfonate as wetting agents.

Dusts are free-flowing admixtures of the active ingredient with finely divided solids such as talc, natural clays, kieselguhr, flours such as walnut shell and cotton seed flours, and other organic and inorganic solids which act as dispersants and carriers for the toxicant; these finely divided solids have an average partical size of less than about 50 microns. A typical dust formulation, useful herein, is one containing 1.0 part of N-(methanesulfonyloxy)-4-methoxybenzimidoyl chloride and 99.0 parts of talc.

Emulsifiable concentrates are homogeneous liquid or paste compositions which are dispersible in water or other dispersant, and may consist entirely of the substituted N-(sulfonyloxy)benzimidoyl halide with a liquid or solid emulsifying agent, or may also contain a liquid carrier, such as xylene, heavy aromatic naphthas, dimethyl sulfoxide, isophorone, and other nonvolatile organic solvents. For application, these concentrates are dispersed in water or other liquid carrier, and normally applied as a spray to the area to be treated. The percentage by weight of the essential active ingredient may vary according to the manner in which the composition is to be applied, but in general comprises 0.5 to 95% of the agricultural composition.

Other useful formulations for agricultural applications include simple solutions of the active ingredient in dispersant in which it is completely soluble at the desired concentration, such as acetone, alkylated naphthalenes, xylene, or other organic solvents.

Typical wetting, dispersing, or emulsifying agents used in agricultural formulations include, for example, the alkyl and alkylaryl sulfonates and sulfates and their sodium salts; and other types of surface-active agents, many of which are available in commerce. The surface-active agent, when used, normally comprises from 1 to 15% by weight of the composition.

These formulations may be applied without further dilution or as dilute solutions, emulsions or suspensions in water or other suitable diluent. The compositions may be applied to the area where treatment is desired by spraying onto the vegetation in the case of liquid compositions, or by distribution from mechanical equipment in the case of solids.

The active compositions of this invention may be formulated or applied with insecticides, nematicides, herbicides, plant growth regulators, fertilizers and other agricultural chemicals. In applying the compositions of this invention, whether alone or with other agricultural chemicals, an effective amount and concentration of the active ingredient N-(sulfonyloxy)benzimidoyl halide are of course employed.

It is apparent that modifications may be made in the formulation and application of the compositions of this invention, without departing from the novel concept as defined in the following claims.

We claim:

1. A method of combatting plant-infesting pathogenic fungi and bacteria which comprises applying to the plants a fungicidally or bactericidally effective amount of a substituted N-(sulfonyloxy)benzimidoyl chloride of the formula:

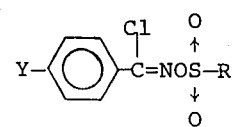

wherein Y is methoxy and R is methyl, ethyl, or propyl.

2. The method of claim 1 wherein the compound is N-(methanesulfonyloxy)-4-methoxybenzimidoyl chloride.

3. A method of combatting plant-infesting pathogenic fungi and bacteria which comprises applying to the plants a fungicidally or bactericidally effective amount of a substituted N-(sulfonyloxy)benzimidoyl chloride of the formula:

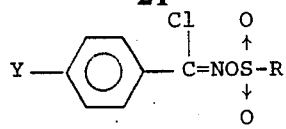

wherein Y is ethoxy and R is methyl, ethyl, or propyl.

4. The method of claim 3 wherein the compound is N-(methanesulfonyloxy)-4-ethoxybenzimidoyl chloride.

5. An agricultural fungicidal composition which comprises, as active ingredient, a fungicidally effective amount of a substituted N-(sulfonyloxy)benzimidoyl chloride of the formula:

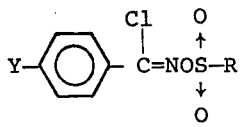

wherein Y is methoxy and R is methyl, ethyl or propyl; in admixture with an agriculturally acceptable carrier, and a surface-active agent.

6. The composition of claim 5 wherein the compound is N-(methanesulfonyloxy)-4-methoxybenzimidoyl chloride.

7. An agricultural fungicidal composition which comprises, as active ingredient, a fungicidally effective amount of a substituted N-(sulfonyloxy)benzimidoyl chloride of the formula:

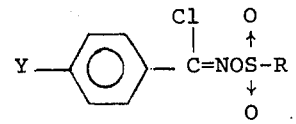

wherein Y is ethoxy and R is methyl, ethyl or propyl; in admixture with an agriculturally acceptable carrier, and a surface-active agent.

8. The composition of claim 7 wherein the compound is N-(methanesulfonyloxy)-4-ethoxybenzimidoyl chloride.

* * * * *

UNITED STATES PATENT OFFICE
CERTIFICATE OF CORRECTION

Patent No. 3,983,246　　　　　　　　Dated September 28, 1976

Inventor(s) Loren K. Gibbons et al.

It is certified that error appears in the above-identified patent and that said Letters Patent are hereby corrected as shown below:

Column 4, line 34, change "other" to --ether--.

Column 5, line 55, change "$C_8H_6CL_3NO_3S$" to --$C_8H_6Cl_3NO_3S$--.

Column 6, line 32, change "ws" to --was--.

Column 6, line 48, change "$C_9H_{10}ClCO_4S$" to --$C_9H_{10}ClNO_4S$--.

Column 6, line 56, change "methylbenzaldoxine" to --methylbenzaldoxime--.

Column 11, line 65, change "precent" to --percent--.

Column 11, Table 1, all numbers following "VI" should be moved over to column beyond that in which they now appear.

Signed and Sealed this

Twelfth Day of April 1977

[SEAL]

Attest:

RUTH C. MASON　　　　　　　　C. MARSHALL DANN
Attesting Officer　　　　　　　Commissioner of Patents and Trademarks